United States Patent
Boriss

(10) Patent No.: US 10,634,663 B2
(45) Date of Patent: Apr. 28, 2020

(54) DETERMINATION OF BINDING CONSTANTS BY MEANS OF EQUILIBRIUM SHIFTING

(71) Applicant: Sovicell GmbH, Leipzig (DE)

(72) Inventor: Hinnerk Boriss, Leipzig (DE)

(73) Assignee: 3B PHARMACEUTICALS GMBH, Berlin (DE)

( * ) Notice: Subject to any disclaimer, the term of this patent is extended or adjusted under 35 U.S.C. 154(b) by 318 days.

(21) Appl. No.: 15/519,510

(22) PCT Filed: Oct. 15, 2015

(86) PCT No.: PCT/EP2015/073902
§ 371 (c)(1),
(2) Date: Apr. 14, 2017

(87) PCT Pub. No.: WO2016/059164
PCT Pub. Date: Apr. 21, 2016

(65) Prior Publication Data
US 2017/0227524 A1      Aug. 10, 2017

(30) Foreign Application Priority Data
Oct. 16, 2014   (DE) .................. 10 2014 115 088

(51) Int. Cl.
*G01N 33/50*   (2006.01)
*G01N 33/543*   (2006.01)
*G01N 33/92*   (2006.01)
*G01N 33/48*   (2006.01)

(52) U.S. Cl.
CPC ............. *G01N 33/50* (2013.01); *G01N 33/48* (2013.01); *G01N 33/54306* (2013.01); *G01N 33/54313* (2013.01); *G01N 33/92* (2013.01)

(58) Field of Classification Search
None
See application file for complete search history.

(56) References Cited

U.S. PATENT DOCUMENTS

| 2004/0166549 A1 | 8/2004 | Karlsson et al. |
| 2007/0111208 A1* | 5/2007 | Schuhmacher .... G01N 33/5432 435/6.16 |
| 2013/0203181 A1 | 8/2013 | Boriss |

FOREIGN PATENT DOCUMENTS

| JP | 2007-510206 A | 4/2007 |
| JP | 2008-503753 A | 2/2008 |
| JP | 2008-503753 | * 3/2008 |
| WO | 2005/017528 A1 | 2/2005 |
| WO | 2011/134860 A1 | 11/2011 |
| WO | 2016/059164 A1 | 4/2016 |

OTHER PUBLICATIONS

Chuang et al. Drug Melab. Pharnnacokinet. 24 (4): 35S-364, 2009.*
Joachim Schuhmacher et al: "High-throughput determination of the free fraction of drugs strongly bound to plasma proteins", Journal of Pharmaceutical Sciences, vol. 93, No. 4, Apr. 1, 2004, pp. 816-830. Washington, U.S.
R. Longhi et al: "Brain Tissue Binding of Drugs: Evaluation and Validation of Solid Supported Porcine Brain Membrane Vesicles (Transil) as a Novel High-Throughput Method", Drug Metabolism Disposition, vol. 39, No. 2, Nov. 11, 2010, pp. 312-321, United States.
Schuhmacher J et al: "Determination of the free fraction and relative free fraction of drugs strongly bound to plasma proteins", Journal of Pharmaceutical Sciences, American Pharmaceutical Association, Washington, U.S., vol. 39, No. 8, Aug. 1, 2000, pp. 1008-1021.
Kim Yumee et al: "A phospholipase A-2 kinetic and binding assay using phospholipid-coated hydrophobic beads", Analytical Biochemistry, Academic Press Inc, New York, vol. 250, No. 1, Jan. 1, 1997, pp. 109-116.
Loidl-Stahlhofen A et al: "Multilamellar liposomes and solid-supported lipid membranes (Transil): screening of lipid-water partitioning toward a high-throughput scale", Pharmaceutical Research, Springer New York LLC, US, vol. 18, No. 12, Dec. 1, 2001, pp. 1782-1788.
Victor Tuan Giam Chuang et al: "Updates on Contemporary Protein Binding Techniques", Drug Metabolism and Pharmacokinetics, vol. 24, No. 4, Jun. 12, 2009, pp. 358-364.
Hartman T et al: "Lipophilicity—beyond octanol/water: a short comparison of modern technologies", Drug Discovery Today: Technologies, Elservier, Amsterdam, NL, vol. 1, No. 4, Dec. 1, 2004, pp. 431-439.
Hong Wan et al: "High-Throughput Screening of Drug-Brain Tissue Binding and in Silico Prediction for Assessment of Central Nervous System Drug Delivery", Journal of Medicinal Chemistry, vol. 50, No. 19, Mar. 29, 2007, pp. 1606-4615.
European Patent Office, International Search Report for PCT Application No: PCT/EP2015/073902, dated Dec. 22, 2015.
European Patent Office, Written Opinion of the International Search Authority for PCT Application No. PCT/PCT/EP2015/073902, dated Dec. 22, 2015.
Japan Patent Office, Notification of Reasons for Rejection Japanese Application No. 2017-520424, dated Apr. 17, 2018.

* cited by examiner

*Primary Examiner* — Michael L Borin
(74) *Attorney, Agent, or Firm* — Socal IP Law Group LLP; Angelo J. Gaz

(57) ABSTRACT

There are disclosed a method for determining binding constants between a substance or a substance mixture and a target, and a kit for carrying out the method according to the invention. The binding constants of the substance for the targets are determined by shifting the binding equilibrium. The concentrations of the immobilised and the dissolved target are varied and the affinities with the targets are determined by shifting the binding equilibria in the individual batches.

16 Claims, No Drawings

DETERMINATION OF BINDING CONSTANTS BY MEANS OF EQUILIBRIUM SHIFTING

The invention relates to a method for determining binding constants between a substance or a substance mixture and a target according to claim 1 and to a kit according to claim 16.

The determination of interactions and binding constants between a substance or a substance mixture and a target plays a major role in the pharmaceutical industry, particularly in pharmacological research and development. Both of these areas involve interactions between a substance or substance mixtures and living beings. Here, it is essential to quantify the binding characteristics of individual substances with binding parameters and binding constants.

A method for determining binding constants is known from DE 102010018 965 A1. In this method, proteins immobilized on solids, for example, are brought into contact with an aqueous solution of the substance to be tested and incubated for a period sufficient for binding of the dissolved substance to the proteins. The solid-supported proteins are then separated from the solution (e.g. by sedimentation). Using suitable measurement methods, the concentration of the substance to be tested in the remaining solution (supernatant), or optionally in the separated solid-supported proteins, is determined, specifically for a plurality of different mixing ratios of the solid-supported proteins to the substance to be tested. For this purpose, identical amounts of the substance to be tested for binding are incubated in uniform solution volumes with different amounts of the solid-supported proteins. The total volume of the liquid phase of the sample to be tested, which consists of the volume of the buffer solution in which the substance or substance mixture to be tested is dissolved, was kept constant in all cases. A drawback of this method is that substances having very high affinities for plastic or glass adhere non-specifically to the sample containers and are thus lost or precipitate out due to low solubility.

Moreover, EP 1658499 A1 describes a method for determining the binding constants or the free fraction of substances in diluted plasma and serum in which the binding of a substance to immobilized membranes (Target 1) and diluted plasma (Target 2) is determined. The drawback of this method is that interactions between substances and targets that show an extremely high or low affinity for membranes cannot be determined. For example, the latter is the case for peptides, which e.g. are conjugated with fatty acids as lipid anchors, while the former is frequently the case for lipids without such anchors.

The object of the present invention is therefore to provide a method for determining binding constants between a substance or a substance mixture and a target that overcomes the drawbacks associated with known methods. In particular, it should be possible to determine binding constants between substances and targets which, in the use of conventional methods, show an extremely high or low affinity for membranes or an extremely high affinity for the sample container. According to a further embodiment, a method is also to be provided in which the binding constants between the substance and the immobilized target and between the substance and the soluble target can be simultaneously determined. A further object of the invention is to provide a kit with which the method according to the invention can be easily and inexpensively carried out.

This object is achieved by the method with the features of claim 1 and a kit with the features of claim 16. Embodiments are subject matter of claims 2 through 15.

The invention relates to a method for determining binding constants of a substance or a substance mixture with respect to a soluble target and an insoluble target, comprising the following steps:

incubation of a first sample of the substance or the substance mixture with a target immobilized on a solid, preferably particulate carrier in a first sample container that contains a buffer solution and a dissolved target, incubation of a second sample of the substance or the substance mixture with the target immobilized on a solid, preferably particulate carrier in a second sample container that contains buffer solution and dissolved target, incubation of a third sample of the substance or the substance mixture with the target immobilized on a solid, preferably particulate carrier in a third sample container that contains buffer solution and dissolved target, incubation of a fourth sample of the substance or the substance mixture with the target immobilized on a solid, preferably particulate carrier in a fourth sample container that contains buffer solution and dissolved target, with it being provided according to the invention that the first and second sample of the substance containing different substance amounts of the immobilized target and the same substance amount of the dissolved target are incubated, and the third and the fourth sample of the substance containing the same substance amounts of the immobilized target as the first and second sample of the substance and containing the same substance amount of the soluble target are incubated, wherein the substance amount of the soluble target in sample containers three and four differs from the substance amount of the soluble target in sample containers one and two, and the sample containers during incubation contain the same volume of liquid phase, composed of buffer solution, dissolved target, and substance sample, and the method according to the invention further comprises the following steps:

separation of the solid, preferably particulate carrier from the respective incubation batches, measurement of the concentration of the substance not bound to the immobilized target or the substance mixture not bound to the immobilized target (APA concentration) in the supernatant of the respective incubation batch, determination of a binding constant of the substance or the substance mixture with respect to the immobilized target and a binding constant of the substance or the substance mixture with respect to the dissolved target based on the measured APA concentrations.

The invention relates in particular to method for determining binding constants between an individual substance and a target. In the sense of the present invention, however, the binding constants can also alternatively be determined for a substance mixture with respect to a target. Here, a substance mixture is to be understood in particular as referring to a mixture containing at least two substances that optionally bind to a target. With the method according to the invention, the binding constant with respect to the target can be determined for each substance in such a substance mixture. This is applied in particular in multiplexing. Unless explicitly differentiated in the following, the use of the term substance also includes the substance mixture.

The basic functional principle of the method according to the invention is determination of the binding constants of the substance for the targets by shifting the binding equilibrium. Here, the concentrations of the two targets, namely the immobilized and the dissolved target, are varied, and the affinities for the targets are determined by the shifting of the binding equilibria in the individual batches.

The method according to the invention is thus used for determining binding constants between a substance or a substance mixture and a target. In the method according to the invention, however, in contrast to the prior art, not only is the concentration of the immobilized target varied, but a second phase is also introduced of the same or a different target in solution, the concentration of which is also varied. The advantage of the method according to the invention is therefore that interactions between a substance or a substance mixture and two different targets can also be determined. Moreover, introduction of the second dissolved target increases the solubility of the substances or substance mixtures. For determination of the binding constants, at least four samples are required: two for different substance amounts of the immobilized target combined with two for different substance amounts of the soluble target. This gives the minimum measured concentration of the substance in the supernatant (free or bound to soluble target) required to determine the binding constants of the substance with respect to the immobilized and dissolved target according to the invention. Because the method according to the invention also comprises a soluble target in addition to the immobilized target, and not only the concentration of the immobilized target, but also that of the soluble target is varied, the method according to the invention makes it possible to simultaneously determine the binding constants between the substance and the immobilized target and the binding constants between the substance and the soluble target.

According to an essential embodiment of present invention, the binding equilibrium is shifted in order to determine the binding constants. In this case, the concentrations of the immobilized target and the dissolved target are varied. The first and the second sample of the substance are incubated with different substance amounts of the immobilized target. This causes the substance amount of the immobilized target in incubation batch one to differ from the substance amount of the immobilized target in incubation batch two. Moreover, the third and the fourth sample of the substance are incubated with a different substance amount of the soluble target. This causes the substance amount of the soluble target in incubation batch three and four to differ from the substance amount of the soluble target in incubation batch one and two. The respective difference in the substance amount required to reach said variation in the concentration of the target can vary in each case, irrespective of one another, in a range of a factor of 1.5 to 100, and particularly 2 to 10.

The third and the fourth sample of the substance are incubated with the same substance amounts of the immobilized target as the first and second sample of the substance. As a result, the substance amount of the immobilized target in incubation batches three and four is therefore varied in the same manner as in incubation batches one and two.

In other words, it follows therefrom that incubation batches one and three contain the same substance amount of the immobilized target. Incubation batches two and four also contain the same substance amount of the immobilized target, but this differs from the substance amount of the immobilized target of incubation batches one and three. Incubation batches one and two contain the same substance amount of the dissolved target, and incubation batches three and four also contain the same substance amount of the dissolved target, but the latter substance amount differs from the substance amount of incubation batches one and two.

In measurement of the APA concentration, the concentration of the substance not bound to the immobilized target or the substance mixture not bound to the immobilized target in the supernatant of the respective incubation batch is determined. The APA concentration is the entire concentration of the substance not bound to the immobilized target or the substance mixture not bound to the immobilized target in the supernatant of the respective incubation batch, i.e. containing the free substance or free substance mixture and the substance or substance mixture bound to the soluble target.

It can be seen that in the method according to the invention, at least four APA concentrations are determined, as at least four sample containers with corresponding incubation batches are used.

A further embodiment of the method according to the invention provides that in addition to the first, second, third, and fourth sample of the substance, at least one further sample of the substance or the substance mixture, preferably between 1 and 21 further samples, is incubated with the target immobilized on a solid, preferably particulate carrier in at least one further sample container containing buffer solution and dissolved target, and preferably in 1-21 further sample containers containing buffer solution, wherein the further samples containing different substance amounts of the immobilized target are incubated, the further samples containing different substance amounts of the dissolved target are incubated, and at least one of the further samples is incubated in two sample containers with the same concentration of immobilized target, and at the same time, different concentrations of the dissolved target and all further sample containers contain the same amount of buffer solution during incubation as the first, second, third, and fourth sample containers. The advantage of the increase in the number of samples is that the error rate decreases with the increasing number of concentration values that can be used for determination.

In order to estimate the binding constants, the immobilized target concentration is optionally varied in 2 to 5 reaction batches respectively, and a constant amount of substance is added. Moreover, a constant volume of the dissolved target (plasma, albumin, etc.) is also added to these reaction batches. Here, it should be noted that the concentration of the target dissolved in the volume can differ due to dilution with buffer. Up to 5 different concentrations of dissolved targets are used in 2 to 5 parallel batches, which gives rise to 4 to 25 reaction batches with different concentrations of immobilized target and dissolved target.

According to a further embodiment in addition to the first, second, third, and fourth substance samples, at least five further samples of the substance or the substance mixture are used (i.e. 9 samples, corresponding to 3 concentration stages of the immobilized target in combination with 3 concentration stages of the soluble target). 25 samples are preferably used. In this case, 5 different substance amounts of the immobilized target are combined with 5 different substance amounts of the soluble target, so that each individual substance amount of the immobilized target is incubated with each substance amount of the soluble target, resulting in 25 different binding equilibria. During incubation, however, the sample containers always contain the same amount of buffer solution as the first, second, third, and fourth sample containers. In order to estimate the binding constants, the target concentration is varied in 25 reaction batches, and a constant amount of substance is added. At least two different concentrations of both targets, i.e. the dissolved and immobilized targets, are thus used.

A further embodiment provides that the concentration of the substance or the substance mixture (APA) in the supernatant of the respective incubation batch is determined relative to a reference sample. In particular, such a reference sample is a sample that contains only buffer solution, soluble target, and the substance or substance mixture to be tested, but not the immobilized target.

In an embodiment of the method according to the invention, the dissolved and the immobilized targets are identical. According to a further variant, the dissolved and the immobilized targets are different.

The target according to the invention should preferably be a target compound or a target receptor. Targets can therefore also be referred to as receptors. For example, active or harmful ingredients can bind to the target. In particular, suitable targets include biological targets such as proteins, preferably enzymes, antibodies, or mixtures such as plasma. Specifically, the targets can be non-membrane-bound proteins or extracellular protein domains responsible for binding such as epidermal growth factor receptor (EGFR) and tumor necrosis factor receptor (TNFR), plasma proteins such as human serum albumin (HSA) or alpha-1-acid glycoprotein (AGP), protein mixtures such as plasma or serum, or tissue homogenates. The targets can be naturally occurring or artificially manufactured targets. It can be seen that the target can be a mixture of different target compounds or target receptors. A common feature of all immobilized targets is that they are immobilized on a solid.

The substance or substance mixture to be tested can also be referred to as a ligand. Such substances to be tested can be peptides, nucleic acids, ribonucleic acids, lipids, and other biomolecules. The substances to be tested can also be chemical substances such as drugs or toxins. The interaction between the target and the substance or substance mixture can involve specific or non-specific bonds. The bonds are generally not covalent. In this case, the test substances compete in bonding to the targets. In contrast to membranes, the use of immobilized targets including proteins such as albumin or antibodies makes it possible to determine interactions between substances and targets that show only an extremely low or an extremely high affinity for membranes. Peptides are an example of such substances.

According to a further embodiment of the method according to the invention, the binding constants to be determined are affinity or dissociation constants.

Determination of the affinity or dissociation constants is carried out in an advantageous embodiment according to equation I:

$$APA = \frac{c_0 \cdot K_D^H \cdot ([P] + K_D^P)}{[immoT] \cdot K_D^P + K_D^H \cdot ([P] + K_D^P)}, \quad (I)$$

wherein

APA is the concentration of the substance that is not bound to the immobilized target, i.e. free substance and substance bound to the soluble target, $K_D^H$ is the dissociation constant of the immobilized target, $K_D^P$ is the dissociation constant of the dissolved target, $c_0$ is the total constant added substance concentration,

[immoT] is the concentration of the immobilized target, and

[P] is the concentration of the dissolved target.

Accordingly, the dissociation constants of the substance with respect to the immobilized target and the dissociation constants of the substance with respect to the dissolved target are determined. It is known that the respective association constants are mathematically derived from the dissociation constants, and vice versa.

In order for this equation to be used, the interactions between substance and targets must follow first-order or approximately first-order binding kinetics.

Determination of the dissociation constants is therefore carried out by means of a method according to one of the aforementioned embodiments, which preferably further comprises the following steps:

use of a matrix of dissociation constants for $K_D^H$ and $K_D^P$ in equation I, calculation of the respective APA concentrations to be expected for the matrix of dissociation constants, comparison of the calculated APA concentrations with the measured APA concentration, selection of the value pair $K_D^H$ and $K_D^P$ that shows the smallest deviation between calculated APA concentration and measured APA concentration as specified dissociation constants of the substance to be tested with respect to the immobilized or the dissolved target.

In a preferred embodiment of this method, selection of the value pair $K_D^H$ and $K_D^P$ that shows the smallest deviation between calculated APA concentration and measured APA concentration is carried out by means of a numerical optimization method.

According to an improvement of the method according to the invention, the binding constants are determined using the aforementioned equation $$APA = \frac{c_0 \cdot K_D^H \cdot ([P] + K_D^P)}{[immoT] \cdot K_D^P + K_D^H \cdot ([P] + K_D^P)},$$

wherein a plurality of binding constant values for $K_D^H$ and $K_D^P$ are first inserted into the equation and the respective APA concentrations to be expected for these values are calculated. The calculated APA concentrations are then compared with the measured APA concentration. In a further step, the smallest deviation between the calculated APA concentration and the measured APA concentration is determined by means of a numerical optimization method, preferably the "least squares" optimization method, and the formula $\gamma = (APA_{measured} - APA_{calculated})^2$. The lowest value for the deviation is selected from these deviations. Next, one selects the corresponding value pair for the binding constants $K_D^H$ and $K_D^P$ to which this value of the lowest deviation is to be assigned. These then constitute the binding constants of the substance to be tested.

According to a preferred embodiment, a matrix of dissociation constants $K_D^H$ and $K_D^P$ can thus be constructed. The matrix is filled with the residuals derived from the measured APA values and the APA values calculated from the $K_D^H$ and $K_D^P$ values of the respective row and column of the matrix according to the following formula:

$$\gamma = (APA_{measured} - APA_{calculated})^2$$

The combination of $K_D^H$ and $K_D^P$ values that gives the smallest deviation constitutes the optimum combination of $K_D^H$ and $K_D^P$ values that best explains the measurement values. The $K_D^H$ and $K_D^H$ values determined in this manner are the binding constants obtained according to the invention.

In one embodiment of the method, a carrier for the immobilized target is provided that is insoluble in an aqueous solution. This allows the carrier to be easily separated from the incubation batch and to be optionally reusable for repeating the method.

In a particularly preferred embodiment, the carrier consists of an organic or inorganic polymer, with agarose being particularly preferred. The advantage of agarose lies in its low non-specific binding of substances to be tested, such as peptides in particular.

According to a further embodiment of the method according to the invention, it is provided that the carrier is in particulate form, with the particles being at least partially micro- or nanoscale particles. In this case, the particles can be magnetic or non-magnetic nanoparticles, silica particles, or sepharose microbeads.

In a particularly preferred embodiment of the method, the carrier is a particulate agarose carrier. A further advantage of such a carrier is that it is commercially available.

Particularly preferred is a variant embodiment of the method according to the invention in which the immobilized target is albumin. Albumin is particularly well-suited as an immobilized target because it can be immobilized according to standard methods.

In a further advantageous embodiment of the method, the soluble target is plasma or serum of human or animal origin. The advantage of plasma or serum lies in the particular physiological relevance of the measurement results.

A further embodiment of the method according to the invention provides that separation of the carrier is carried out by filtration, centrifugation, or decanting of the buffer solution. Such methods allow the carrier to be separated from the incubation batch without increasing the time and costs required.

In a preferred embodiment, the carrier is in particulate form, and the particles have magnetic properties. In this case, an embodiment according to the invention is provided in which the carrier is separated by applying a magnetic field to detach it. The use of magnetic particles and magnetic separation offers considerable advantages over other technologies. The magnetic particles can be directly and selectively isolated from the incubation batch and purified. Compared to conventional separation methods, magnetic separation is simple and fast. In addition, steps such as changing the buffer or washing steps can be carried out in a simple manner.

Particularly preferably, measurement of the concentration of the substance or the substance mixture is carried out by mass spectrometry, fluorescence spectroscopy, methods using radioactivity, or chromatography methods or a combination of such methods. These methods can be widely varied, and can be correspondingly adapted and modified according to the test substance. In this way, each concentration of the substance can be determined as precisely as possible.

According to a further embodiment of the method according to the invention, the buffer solution is an aqueous saline solution. Such solutions are particularly well-suited for testing binding constants, as the targets used are stable therein and the solutions are commercially available.

In a particularly preferred embodiment of the method according to the invention, the sample containers are cavities of microtiter plates or in particular have surface properties that do not interfere with the substance or the substance mixture.

The invention further relates to a kit for determining binding constants between a substance or a substance mixture and a target by a method according to one of the above-mentioned embodiments. Here, the invention provides that the kit according to the invention contains at least 4 sample containers or at least 4 cavities of a microtiter plate, buffer solution, an amount of a dissolved target, and an amount of a target immobilized on a solid, preferably particulate carrier, wherein the dissolved and the immobilized targets can be identical or different.

According to a further embodiment of the invention, the method for determining binding constants of a substance or a substance mixture with respect to a soluble target and an immobilized target according to one of the above-mentioned embodiments is configured such that in particular, determination of a binding constant of the substance or the substance mixture with respect to the immobilized target and a binding constant of the substance or the substance mixture with respect to the dissolved target is carried out based on the measured APA concentrations by executing a computer program. A further embodiment of the invention thus relates to a computer program for determining binding constants of a substance or a substance mixture with respect to a soluble target and an immobilized target that is configured such that determination of a binding constant of the substance or the substance mixture with respect to the immobilized target and a binding constant of the substance or the substance mixture with respect to the dissolved target can be carried out based on the measured APA concentrations. A further embodiment of the invention relates to a computer program product such as a data carrier, a storage medium, or a machine-readable medium than can be read by such a computer program. If necessary, the above-mentioned kit can additionally comprise such a computer program product.

Further features, details, and advantages of the invention are specified in the wording of the claims and the following description of exemplary embodiments, wherein the invention is not limited to one of the embodiments described, but can be used in a wide variety of ways. In this case, all features and advantages derived from the claims, the description, and the drawing, including design details, spatial arrangements, and process steps, can be essential to the invention, both individually and in the widest variety of combinations.

Exemplary Embodiment 1

A) Experimental Design

A particularly preferred embodiment is a microtiter plate in which 5 columns with 7 cavities are used for the above-described method, so that 25 samples with immobilized target and 10 samples as references without immobilized target are incubated. Human serum albumin (HSA) was used as immobilized target (Target 1). The HSA was immobilized according to a standard method on commercial sepharose beads (Mini-Leak beads medium, Kem-En-Tec Nordic A/S). Human plasma was used as a soluble target. The substance to be tested is a peptide. 5 concentrations of immobilized HSA are used for each of 5 plasma concentrations. For this purpose, the cavities of a microtiter plate are filled as follows:

Column I of the microtiter plate (using lines 1 through 7):

| | Cavity | | | | | | |
|---|---|---|---|---|---|---|---|
| | I-1 Ref 1 | I-2 Ref2 | I-3 V1 HSA | I-4 V2 HSA | I-5 V3 HSA | I-6 V4 HSA | I-7 V5 HSA |
| HSA concentration in μM | 0 | 0 | 11 | 21 | 37 | 67 | 120 |
| Volume of bead suspension in μL | 0 | 0 | 36 | 64 | 115 | 208 | 374 |
| Buffer volume in μL | 290 | 290 | 265 | 246 | 212 | 148 | 35 |
| Volume of beads in μL | 0 | 0 | 11 | 20 | 37 | 66 | 119 |
| Sample volume in μL | 10 | 10 | 10 | 10 | 10 | 10 | 10 |
| Volume of pure plasma in μL | 150 | 150 | 150 | 150 | 150 | 150 | 150 |

Column II of the microtiter plate (using lines 1 through 7):

| | Cavity | | | | | | |
|---|---|---|---|---|---|---|---|
| | II-1 Ref 1 | II-2 Ref2 | II-3 V1 HSA | II-4 V2 HSA | II-5 V3 HSA | II-6 V4 HSA | II-7 V5 HSA |
| HSA concentration in μM | 0 | 0 | 11 | 21 | 37 | 67 | 120 |
| Volume of bead suspension in μL | 0 | 0 | 36 | 64 | 115 | 208 | 374 |
| Buffer volume in μL | 290 | 290 | 265 | 246 | 212 | 148 | 35 |
| Volume of beads in μL | 0 | 0 | 11 | 20 | 37 | 66 | 119 |
| Sample volume in μL | 10 | 10 | 10 | 10 | 10 | 10 | 10 |
| Volume of 1:2 diluted plasma in μL | 150 | 150 | 150 | 150 | 150 | 150 | 150 |

Column III of the microtiter plate (using lines 1 through 7):

| | Cavity | | | | | | |
|---|---|---|---|---|---|---|---|
| | III-1 Ref 1 | III-2 Ref2 | III-3 V1 HSA | III-4 V2 HSA | III-5 V3 HSA | III-6 V4 HSA | III-7 V5 HSA |
| HSA concentration in μM | 0 | 0 | 11 | 21 | 37 | 67 | 120 |
| Volume of bead suspension in μL | 0 | 0 | 36 | 64 | 115 | 208 | 374 |
| Buffer volume in μL | 290 | 290 | 265 | 246 | 212 | 148 | 35 |
| Volume of beads in μL | 0 | 0 | 11 | 20 | 37 | 66 | 119 |
| Sample volume in μL | 10 | 10 | 10 | 10 | 10 | 10 | 10 |
| Volume of 1:4 diluted plasma in μL | 150 | 150 | 150 | 150 | 150 | 150 | 150 |

Column IV of the microtiter plate (using lines 1 through 7):

| | Cavity | | | | | | |
|---|---|---|---|---|---|---|---|
| | IV-1 Ref 1 | IV-2 Ref2 | IV-3 V1 HSA | IV-4 V2 HSA | IV-5 V3 HSA | IV-6 V4 HSA | IV-7 V5 HSA |
| HSA concentration in μM | 0 | 0 | 11 | 21 | 37 | 67 | 120 |
| Volume of bead suspension in μL | 0 | 0 | 36 | 64 | 115 | 208 | 374 |
| Buffer volume in μL | 290 | 290 | 265 | 246 | 212 | 148 | 35 |
| Volume of beads in μL | 0 | 0 | 11 | 20 | 37 | 66 | 119 |
| Sample volume in μL | 10 | 10 | 10 | 10 | 10 | 10 | 10 |
| Volume of 1:8 diluted plasma in μL | 150 | 150 | 150 | 150 | 150 | 150 | 150 |

Column V of the microtiter plate (using lines 1 through 7):

| | Cavity | | | | | | |
|---|---|---|---|---|---|---|---|
| | V-1 Ref 1 | V-2 Ref2 | V-3 V1 HSA | V-4 V2 HSA | V-5 V3 HSA | V-6 V4 HSA | V-7 V5 HSA |
| HSA concentration in μM | 0 | 0 | 11 | 21 | 37 | 67 | 120 |
| Volume of bead suspension in μL | 0 | 0 | 36 | 64 | 115 | 208 | 374 |
| Buffer volume in μL | 290 | 290 | 265 | 246 | 212 | 148 | 35 |

-continued

Column V of the microtiter plate (using lines 1 through 7):

| | Cavity | | | | | | |
|---|---|---|---|---|---|---|---|
| | V-1 Ref 1 | V-2 Ref2 | V-3 V1 HSA | V-4 V2 HSA | V-5 V3 HSA | V-6 V4 HSA | V-7 V5 HSA |
| Volume of beads in μL | 0 | 0 | 11 | 20 | 37 | 66 | 119 |
| Sample volume in μL | 10 | 10 | 10 | 10 | 10 | 10 | 10 |
| Volume of 1:16 diluted plasma in μL | 150 | 150 | 150 | 150 | 150 | 150 | 150 |

Here, the plasma is prediluted according to the following table and added to the respective cavities:

| Plasma dilution | Plasma volume and concentration | Addition to the cavities of the columns |
|---|---|---|
| 1:3 | 150 μL pure plasma | Column I |
| 1:6 | 150 μL Plasma[1] in 1:2 Predilution | Column II |
| 1:12 | 150 μL Plasma[1] in 1:4 Predilution | Column III |
| 1:24 | 150 μL Plasma[1] in 1:8 Predilution | Column IV |
| 1:48 | 150 μL Plasma[1] in 1:16 Predilution | Column V |

[1]In calculating the dissociation constants, it is arbitrarily assumed that whole plasma has a concentration of 600 μM. This assumption approximates reality, but is unproblematic, as the calculated dissociation constant refers to this concentration, and correct binding values in the sense of the percentage of plasma-bound substance are therefore obtained even if the "true" concentration is different.

It can be seen that the principle according to the invention of changing the concentrations of the two targets, i.e. the immobilized and the dissolved targets, is implemented here. A first and a second sample of the substance containing different substance amounts of the immobilized target and the same substance amount of the dissolved target are incubated (e.g. cavity I-3 and I-7 with an immobilized HSA concentration of 11 μM or 120 μM, wherein both cavities contain 1:3 diluted plasma). Moreover, a third and a fourth sample of the substance with the same substance amounts of the immobilized target as the first and second sample of the substance and containing the same substance amount of the soluble target are incubated (e.g. cavity V-3 and V-7 with an immobilized HSA concentration of 11 μM or 120 μM, wherein both cavities contain 1:48 diluted plasma), wherein the substance amounts of the soluble target in sample containers three and four differ from the substance amount of the soluble target in sample containers one and two.

B) Experimental Method

10 μL each of a 10 to 2000 μM stock solution of the test substances is added to the cavities. In this example, a 1012.5 μM stock solution of the peptide was used. After addition of 10 μL to the above-described experimental setup, the concentration of the peptide in all of the cavities was 22.5 μM. After mixing by resuspension of the beads on which target 1 (here human serum albumin) is immobilized, the target fixed on the carrier material is separated. For this purpose, the microtiter place is centrifuged so that the beads undergo sedimentation. The concentration in the supernatant is determined by means of suitable methods, such as LC/MS/MS or scintillation counting. The unbound fraction of the substance is determined in cavities with the immobilized target relative to the reference samples. This obviates the need for calibration, as long as the signal to concentration ratio for the test substances and the quantitation system used follow a linear course.

C) Evaluation of the Experiment

If one multiplies the concentrations measured for all 25 samples relative to the reference samples by the concentrations of the test substance used in the experiment (here 22.5 μM), one obtains the APA concentrations in all 25 samples (shown in column 3). According to the above-mentioned formula for APA, the APA values to be expected can be calculated from the dissociation constants $K_D^H$ and $K_D^P$. In order to determine these dissociation constants, a commonly known numerical "least squares" optimization method is used. The configuration of this method can differ widely. For this example, a matrix of dissociation constant $K_D^H$ ranging from $1.9*10^{-5}$ to $1.1*10^{-7}$ μM and dissociation constant $K_D^P$ ranging from $6.0*10^{-4}$ to $1.8*10^{-11}$ μM was constructed. The matrix was filled with the residuals derived from the measured APA values and the APA values calculated from the $K_D^H$ and $K_D^P$ values of the respective row and column of the matrix according to the following formula:

$$\gamma = (APA_{measured} - APA_{calculated})^2$$

The combination of $K_D^H$ and $K_D^P$ values that gives the smallest deviation constitutes the optimum combination of $K_D^H$ and $K_D^P$ values that best explains the measurement values. The $K_D^H$ and $K_D^P$ values determined in this manner are taken as the result for the binding constants. The APA values calculated from this value combination are shown in column 4 of the following table, and the residuals are shown in column 5.

| | 1 Concentration of human plasma [P] in [μM] | 2 Immobilized HSA concentration [μM] | 3 Measured APA concentration [μM] | 4 Predicted APA concentration with optimum constants [μM] | 5 Residuals |
|---|---|---|---|---|---|
| Column 1: | 200 | 11.4 | 20.8280 | 19.861 | 0.00277 |
| | 200 | 20.6 | 20.9611 | 18.157 | 0.02748 |
| | 200 | 37.0 | 17.2881 | 15.729 | 0.01665 |
| | 200 | 66.7 | 14.4100 | 12.677 | 0.04559 |
| | 200 | 120.0 | 10.2862 | 9.395 | 0.04305 |
| Column II: | 100 | 11.4 | 20.7373 | 18.074 | 0.02555 |
| | 100 | 20.6 | 19.6240 | 15.617 | 0.08655 |
| | 100 | 37.0 | 15.4196 | 12.546 | 0.11166 |
| | 100 | 66.7 | 11.7731 | 9.267 | 0.26716 |
| | 100 | 120.0 | 6.1804 | 6.302 | 0.00492 |
| Column III: | 50 | 11.4 | 19.3799 | 15.810 | 0.06874 |
| | 50 | 20.6 | 16.5692 | 12.772 | 0.16304 |
| | 50 | 37.0 | 12.0566 | 9.489 | 0.25492 |
| | 50 | 66.7 | 7.0854 | 6.488 | 0.08551 |
| | 50 | 120.0 | 3.8316 | 4.134 | 0.18473 |
| Column IV: | 25 | 11.4 | 16.7864 | 13.509 | 0.10571 |
| | 25 | 20.6 | 13.0066 | 10.237 | 0.21905 |
| | 25 | 37.0 | 7.4661 | 7.129 | 0.02034 |
| | 25 | 66.7 | 4.1302 | 4.609 | 0.32078 |
| | 25 | 120.0 | 2.7004 | 2.817 | 0.11962 |
| Column V: | 12.5 | 11.4 | 13.4437 | 11.643 | 0.06701 |
| | 12.5 | 20.6 | 8.5339 | 8.400 | 0.00176 |
| | 12.5 | 37.0 | 4.7166 | 5.595 | 0.56109 |
| | 12.5 | 66.7 | 2.9723 | 3.495 | 1.28026 |
| | 12.5 | 120.0 | 2.3312 | 2.085 | 1.29411 |

For this example, the dissociation constants of the example substance determined in this manner are $K_D^H$=18.7 μM and $K_D^H$=7.3 μM. The fraction of the peptide used bound to whole human plasma is then determined according to the following generally known formula, $$f_b = 1 - \frac{1}{1 + [P]/K_D^P}$$

where [P] is the arbitrarily selected plasma concentration and $K_D^P$ is the value, obtained by the optimization method, of the dissociation constant of the peptide from the plasma. In this example, the fraction of the peptide bound to whole human plasma (undiluted) is 97%. This means that only 3% of the peptide dissolved in the plasma is in free, or unbound, form.

Exemplary Embodiment 2

A) Experimental Design

A particularly preferred embodiment is a microtiter plate in which 5 columns with 7 cavities are used for the above-described method, so that 25 samples with immobilized target and 10 samples as references without immobilized target are incubated. Human serum albumin (HSA) was used as the immobilized target (Target 1). The HSA was immobilized according to standard methods on commercial sepharose beads (Mini-Leak beads medium, Kem-En-Tec Nordic A/S). Human plasma was used as the soluble target. The substance to be tested is the peptide liraglutide. 5 concentrations of immobilized HSA are used for each of 5 plasma concentrations. For this purpose, the cavities of a microtiter plate are filled as follows:

| | Cavity | | | | | | |
|---|---|---|---|---|---|---|---|
| | I-1 Ref 1 | I-2 Ref2 | I-3 V1 HSA | I-4 V2 HSA | I-5 V3 HSA | I-6 V4 HSA | I-7 V5 HSA |
| HSA concentration in μM | 0 | 0 | 11 | 21 | 37 | 67 | 120 |
| Volume of bead suspension in μL | 0 | 0 | 36 | 64 | 115 | 208 | 374 |
| Buffer volume in μL | 290 | 290 | 265 | 246 | 212 | 148 | 35 |
| Volume of beads in μL | 0 | 0 | 11 | 20 | 37 | 66 | 119 |
| Sample volume in μL | 10 | 10 | 10 | 10 | 10 | 10 | 10 |
| Volume of pure plasma in μL | 150 | 150 | 150 | 150 | 150 | 150 | 150 |

Here, the plasma is prediluted according to the following table and added to the respective cavities:

| Plasma dilution | Plasma volume and concentration | Addition to the cavities of the columns |
|---|---|---|
| 1:3 | 150 μL pure plasma | Column I |
| 1:6 | 150 μL Plasma[1] in 1:2 Predilution | Column II |
| 1:12 | 150 μL Plasma[1] in 1:4 Predilution | Column III |
| 1:24 | 150 μL Plasma[1] in 1:8 Predilution | Column IV |
| 1:48 | 150 μL Plasma[1] in 1:16 Predilution | Column V |

[1]In calculating the dissociation constants, it is arbitrarily assumed that whole plasma has a concentration of 600 μM. This assumption approximates reality, but is unproblematic, as the calculated dissociation constant refers to this concentration, and correct binding values in the sense of the percentage of plasma-bound substance are therefore obtained even if the "true" concentration is different.

It can be seen that the principle according to the invention of changing the concentrations of the two targets, i.e. the immobilized and the dissolved targets, is implemented here. A first and a second sample of the substance containing different substance amounts of the immobilized target and the same substance amount of the dissolved target are incubated (e.g. cavity V-3 and V-6), and a third and a fourth sample of the substance with the same substance amounts of the immobilized target as the first and second sample of the substance and a different substance amount of the soluble target (e.g. cavity IV3 and V3) are incubated.

B) Experimental Method

10 μL each of a 0.022 μM stock solution of the test substance liraglutide is added to the cavities. After addition of 10 μL to the above-described experimental setup, the concentration of the peptide in all of the cavities was 22 nM. After mixing by resuspension of the beads on which target 1 (here human serum albumin) is immobilized, the target fixed on the carrier material is separated. For this purpose, the microtiter place is centrifuged so that the beads undergo sedimentation. The concentration in the supernatant is determined by means of suitable methods, such as LC/MS/MS or scintillation counting. The unbound fraction of the substance is determined in cavities with the immobilized target relative to the reference samples. This obviates the need for calibration, as long as the signal to concentration ratio for the test substances and the quantitation system used follow a linear course.

C) Evaluation of the Experiment

If one multiplies the concentrations measured for all 25 samples relative to the references by the concentrations of the test substance used in the experiment (here 22 nM), one obtains the APA concentrations in all 25 samples (shown in column 3). According to the above formula for APA, the APA values to be expected can be calculated from the dissociation constants $K_D^H$ and $K_D^P$. In order to determine these dissociation constants, a commonly known numerical "least squares" optimization method is used. The configuration of this method can differ widely. For this example, a matrix of dissociation constant $K_D^H$ ranging from $1.9*10^{-5}$ to $1.1*10^{-7}$ μM and dissociation constant $K_D^P$ ranging from $6.0*10^{-4}$ to $1.8*10^{-4}$ μM was constructed. The matrix was filled with the residuals derived from the measured APA values and the APA values calculated from the $K_D^H$ and $K_D^P$ values of the respective row and column of the matrix according to the following formula:

$$\gamma = (APA_{measured} - APA_{calculated})^2$$

The combination of $K_D^H$ and $K_D^P$ values that gives the smallest deviation constitutes the optimum combination of $K_D^H$ and $K_D^P$ values that best explains the measurement values. The $K_D^H$ and $K_D^P$ values determined in this manner are taken as the result for the binding constants. The APA values calculated from this value combination are shown in column 4 of the following table, and the residuals are shown in column 5.

| | 1 Concentration of human plasma [P] in [μM] | 2 Immobilized HSA concentration [μM] | 3 Measured APA concentration [μM] | 4 Predicted APA concentration with optimum constants [μM] | 5 Residuals |
|---|---|---|---|---|---|
| Column I: | 200 | 11.4 | 19.9 | 22 | −2.1 |
| | 200 | 20.6 | 20.2 | 21.8 | −1.6 |
| | 200 | 37.0 | 20.5 | 21.5 | −1 |
| | 200 | 66.7 | 19.3 | 20.9 | −1.7 |
| | 200 | 120.0 | 17.2 | 20 | −2.8 |
| Column II: | 100 | 11.4 | 21.1 | 21.8 | −0.7 |
| | 100 | 20.6 | 22.1 | 21.4 | 0.6 |
| | 100 | 37.0 | 19.9 | 20.9 | −1 |
| | 100 | 66.7 | 18.5 | 19.9 | −1.4 |
| | 100 | 120.0 | 18.4 | 18.3 | 0 |
| Column III: | 50 | 11.4 | 20.8 | 21.4 | −0.6 |
| | 50 | 20.6 | 20.9 | 20.8 | 0.1 |
| | 50 | 37.0 | 19.2 | 19.8 | −0.6 |
| | 50 | 66.7 | 17.2 | 18.2 | −1.1 |
| | 50 | 120.0 | 16.3 | 15.9 | 0.3 |
| Column IV: | 25 | 11.4 | 21.0 | 20.8 | 0.1 |
| | 25 | 20.6 | 19.6 | 19.8 | −0.2 |
| | 25 | 37.0 | 17.8 | 18.3 | −0.5 |
| | 25 | 66.7 | 16.1 | 16 | 0.1 |
| | 25 | 120.0 | 14.7 | 13.1 | 1.6 |
| Column V: | 12.5 | 11.4 | 19.5 | 20 | −0.6 |
| | 12.5 | 20.6 | 18.8 | 18.6 | 0.2 |
| | 12.5 | 37.0 | 15.3 | 16.4 | −1.1 |
| | 12.5 | 66.7 | 12.8 | 13.6 | −0.8 |
| | 12.5 | 120.0 | 10.5 | 10.4 | 0.2 |

For this example, the dissociation constants of liraglutide, a peptide, determined in this manner are $K_D^H=7.53$ μM and $K_D^H=36.9$ μM. The fraction of the peptide used bound to whole human plasma is then determined according to the following generally known formula, $$f_b = 1 - \frac{1}{1+[P]/K_D^P}$$

where [P] is the arbitrarily selected plasma concentration and $K_D^P$ is the value, obtained by the optimization method, of the dissociation constant of the peptide from the plasma. In this example, the fraction of the peptide bound to whole human plasma (undiluted) is 98.8%. This means that only 1.2% of the peptide dissolved in the plasma is in free, or unbound, form.

The invention claimed is:

1. A method for determining binding constants of a substance with respect to a dissolved target and an immobilized target, comprising:
incubating a first sample of the substance with a target immobilized on a first solid particulate carrier in a first sample container that contains a buffer solution and a dissolved target,
incubating a second sample of the substance with the target immobilized on a second solid particulate carrier in a second sample container that contains buffer solution and dissolved target,
incubating a third sample of the substance with the target immobilized on a third solid particulate carrier in a third sample container that contains buffer solution and dissolved target,
incubating a fourth sample of the substance with the target immobilized on a fourth solid particulate carrier in a fourth sample container that contains buffer solution and dissolved target,
wherein the first sample and second sample contain different amounts of the immobilized target and a same amount of the dissolved target, and the third sample and the fourth sample contain same amounts of the immobilized target as the first sample and the second sample and contain a same amount of the dissolved target;
wherein the amount of the dissolved target in the third sample container and the fourth sample container differs from the amount of the dissolved target in the first sample container and the second sample container, and
wherein the first sample container, the second sample container, the third sample container and the fourth sample container during incubation contain the same volume of liquid phase, composed of buffer solution, dissolved target, and substance sample,
the method further comprising:
separating the solid particulate carrier from the respective incubation batches,
measuring the APA concentration of the substance not bound to the immobilized target in the supernatant of the respective incubation batch of the first, second, third and fourth containers,
determining a binding constant of the substance with respect to the immobilized target and a binding constant of the substance with respect to the dissolved target based on the measured APA concentrations of the first, second, third and fourth containers;
wherein the binding constants are dissociation constants and determination of the dissociation constants is carried out in equation I for each of the first, second, third and fourth containers:

$$APA = \frac{c_0 \cdot K_D^H \cdot ([P]+K_D^P)}{[immoT] \cdot K_D^P + K_D^H \cdot ([P]+K_D^P)} \quad (I)$$

wherein
APA is a concentration of the substance that is not bound to the immobilized target,
$K_D^H$ is dissociation constant of the immobilized target,
$K_D^P$ is dissociation constant of the dissolved target,
$c_0$ is total constant added substance concentration,
[immoT] is concentration of the immobilized target, and
[P] is concentration of the dissolved target.

2. The method of claim 1 wherein determining the dissociation constants further comprises:
using a matrix of dissociation constants for $K_D^H$ and $K_D^P$ in equation I,
calculating respective APA concentrations to be expected for the matrix of dissociation constants,
comparing the calculated APA concentrations with the measured APA concentration,
selecting a value pair $K_D^H$ and $K_D^P$ that shows the smallest deviation between calculated APA concentration and measured APA concentration as specified dissociation constants of the substance to be tested with respect to the immobilized or the dissolved target.

3. The method of claim 2 comprising selecting the value pair $K_D^H$ and $K_D^P$ that shows the smallest deviation between calculated APA concentration and measured APA concentration numerical optimization.

4. The method of claim 1 further comprising incubating between one and twenty-one further samples with the target immobilized on a solid particulate carrier in at least one further sample container containing buffer solution and dissolved target, and preferably in respective further sample containers containing buffer solution,
- wherein at least one of the further samples is incubated in two sample containers with the same concentration of immobilized target, and at the same time, different concentrations of dissolved target, and
- wherein all further sample containers contain the same amount of buffer solution during incubation as the first, second, third, and fourth sample containers.

5. The method of claim 1 wherein the concentration of the substance (APA) in the supernatant of the respective incubation batch is determined relative to a reference sample.

6. The method of claim 1 wherein the dissolved and the immobilized target are identical or different.

7. The method of claim 1 wherein the carrier is insoluble in an aqueous solution.

8. The method of claim 1 wherein the carrier is composed of an organic or inorganic polymer.

9. The method of claim 1 wherein the carrier is in particulate form, wherein the particles are at least partially micro- or nanoscale particles.

10. The method of claim 1 wherein the immobilized target is albumin.

11. The method of claim 1 wherein the dissolved target is plasma or serum of human or animal origin.

12. The method of claim 1 wherein separating the carrier comprises applying a magnetic field to detach the carrier.

13. The method of claim 1 wherein measuring the concentration of the substance comprises at least one of mass spectrometry, fluorescence spectroscopy, methods using radioactivity, or chromatography methods or a combination of these methods.

14. The method of claim 1 wherein the sample containers are cavities of microtiter plates or have surface characteristics that do not interfere with the substance.

15. The method of claim 8 wherein the carrier is composed of agarose.

16. The method of claim 1, wherein:
- the first sample and second sample contain a first and a second amount of the immobilized target, respectively;
- the first sample and second sample contain a third amount of the dissolved target,
- the third sample and the fourth sample contain the first and the second amount of the immobilized target, respectively;
- the third sample and the fourth sample contain a fourth amount of the dissolved target;
- the first amount is different than the second amount; and
- the third amount is different than the fourth amount.

* * * * *